United States Patent [19]

Amiet

[11] Patent Number: 4,879,407

[45] Date of Patent: Nov. 7, 1989

[54] PROCESS FOR THE PREPARATION OF ETHYL TRIFLUOROACETATE

[75] Inventor: Louis Amiet, Lyons, France

[73] Assignee: Rhone-Poulenc Chimie, Cedex, France

[21] Appl. No.: 109,052

[22] Filed: Oct. 16, 1987

[30] Foreign Application Priority Data

Oct. 16, 1986 [FR] France ................... 86 14606

[51] Int. Cl.$^4$ ..................... C07C 69/63; B01D 3/34
[52] U.S. Cl. ................... 560/227; 203/61; 203/66; 203/82; 203/DIG. 6
[58] Field of Search ............ 560/227; 203/61, 66, 203/82, DIG. 6

[56] References Cited

U.S. PATENT DOCUMENTS

| | | | |
|---|---|---|---|
| 3,290,357 | 12/1966 | Fein et al. | 560/227 |
| 4,701,551 | 10/1987 | DesBois et al. | 560/227 |
| 4,730,082 | 3/1988 | Amiet | 560/227 |

FOREIGN PATENT DOCUMENTS 0209157  1/1987  European Pat. Off. ............ 560/227

OTHER PUBLICATIONS

Norton, T., "A New Synthesis of Ethyl Trifluoroacetate", J.O.C.S., vol. 72, pp. 3527-3528.

"Process for Manufacturing Anhydrous Esters of Trifluoroacetic Acid", Research Disclosure, Aug. 1984. Research Disclosure No. 24432 (1984).

*Primary Examiner*—William R. Dixon, Jr.
*Assistant Examiner*—Anthony J. Green
*Attorney, Agent, or Firm*—Finnegan, Henderson, Farabow, Garrett and Dunner

[57] ABSTRACT

A process for the preparation of ethyl trifluoroacetate, in which:

in a first stage, trifluoroacetic acid is brought into contact with a slight excess of ethanol in the presence of concentrated sulfuric acid and a solvent, the solvent having a boiling point higher than that of trifluoroacetic acid and specific gravity relative to water less than 1 and which solvent does not form an azeotrope with ethyl trifluoroacetate, and then carrying out a phase separation and removing the sulfuric layer, followed, if required, by an additional stage in which concentrated sulfuric acid is added to complete the esterification;

in a second stage, an additional quantity of sulfuric acid and trifluoroacetic acid is introduced and a phase separation is then carried out to remove the sulfuric layer; and in a third stage, the mixture obtained in the second stage is distilled to recover ethyl trifluoroacetate.

39 Claims, 2 Drawing Sheets

PROCESS FOR THE PREPARATION OF ETHYL TRIFLUOROACETATE

BACKGROUND OF THE INVENTION

The present invention relates to a process for the preparation of ethyl trifluoroacetate. It relates more particularly to a process for the preparation of ethyl trifluoroacetate having a high purity.

Preparation of ethyl trifluoroacetate is described in the publication: Research Disclosure No. 24432. This publication discloses the preparation of trifluoroacetic acid esters by a 4-stage process according to which:

an alcohol of formula ROH, in which R represents an alkyl radical containing 1 to 5 carbon atoms, is condensed with trifluoroacetic acid in the presence of a strong inorganic acid (HCl, $H_2SO_4$ or $H_3PO_4$) at a temperature from 25° to 110° C.;

the mixture obtained is cooled and the aqueous phase is removed;

the organic phase is treated with concentrated sulfuric acid and/or phosphoric acid and the reaction between the acid and the alcohol is then continued at 25°-110° C.; and the ester is isolated by distillation.

It has been found that when the reaction is carried out starting with trifluoroacetic acid and ethanol, this process does not enable an ester with a purity greater than 99% to be obtained in an economically profitable manner.

In fact, the esterification reaction is a balanced reaction according to the reaction scheme below:

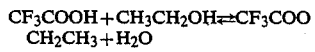

To shift the equilibrium, an excess of one or the other of the starting materials may be used.

If an excess of ethanol is used, it can no longer be completely separated from the ethyl trifluoroacetate obtained because it forms an azeotrope with the latter which has a boiling point close to that of ethyl trifluoroacetate. If an excess of trifluoroacetic acid is used, the excess dissolves in part in the aqueous phase containing sulfuric acid, from which the trifluoroacetic acid is virtually impossible to extract when sulfuric acid is employed in small quantities. Since trifluoroacetic acid is an expensive starting material, it is advantageous to minimize its loss.

Consequently, the industry has been seeking for some time an economically profitable process for the preparation of pure ethyl trifluoroacetate.

SUMMARY OF THE INVENTION

The present invention enables the above object to be achieved. It relates to a process for the preparation of ethyl trifluoroacetate comprising three stages. The first stage includes contacting trifluoroacetic acid with a slight excess of ethanol in the presence of concentrated sulfuric acid and a solvent for a time sufficient to achieve a first esterification. The solvent has a boiling point higher than that of trifluoroacetic acid and a specific gravity relative to water less than 1 and does not form an azeotrope with ethyl trifluoroacetate. A phase separation is then carried out to remove the sulfuric layer, followed, if required, by again adding concentrated sulfuric acid to complete the first esterification.

The second stage includes introducing an additional quantity of sulfuric acid and trifluoroacetic acid for a time sufficient to achieve a second esterification and then carrying out a phase separation to remove the sulfuric layer.

The third stage includes distilling the mixture obtained in the second stage to recover ethyl trifluoroacetate of a high purity.

This process is a significant improvement over the process described in Research Disclosure No. 24432 in that it enables an ester which has a purity greater than 99% to be obtained.

DETAILED DESCRIPTION OF THE PREFERRED EMBODIMENTS

Figure 1:
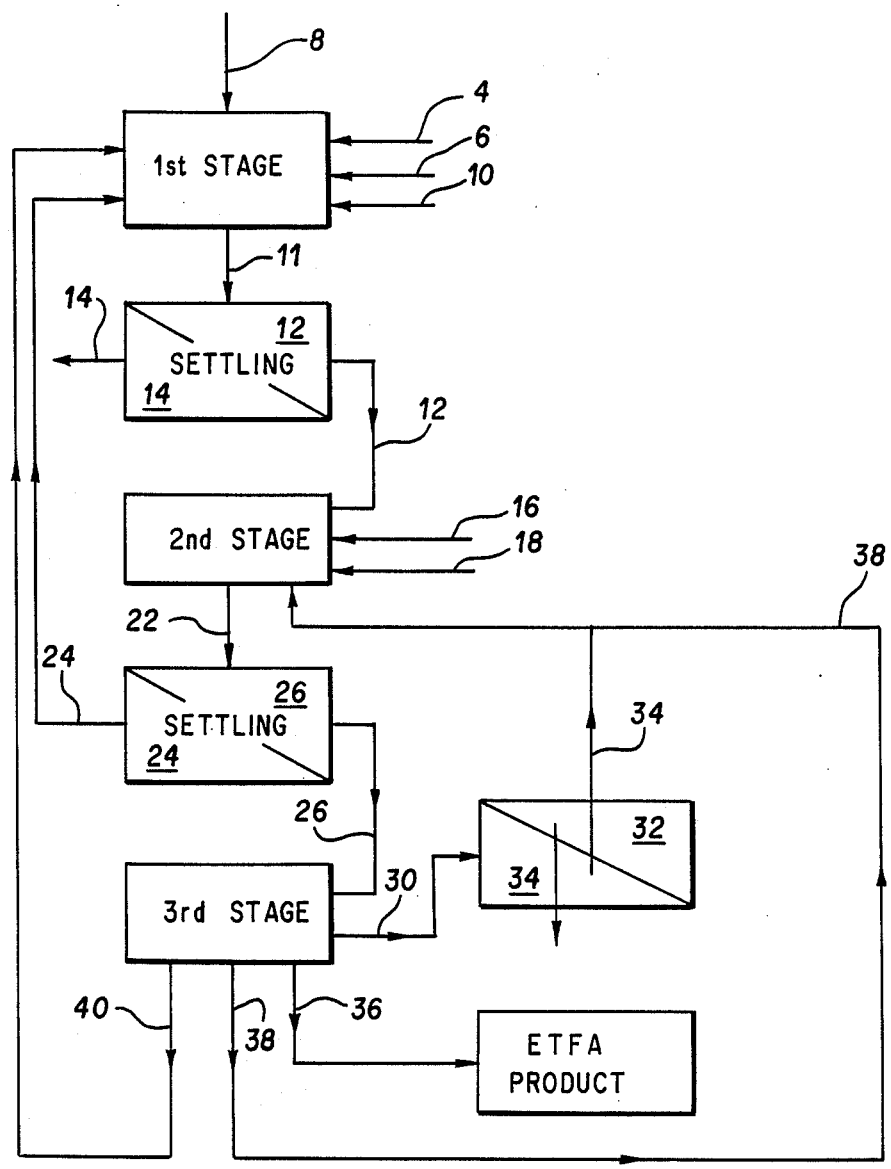
FIG. 1 is a flow diagram of the process of the present invention illustrating a first embodiment having two esterification stages.

Reference will now be made in detail to the present preferred embodiments of the invention as illustrated in the accompanying drawings wherein like reference numerals refer to corresponding parts.

In accordance with the present invention there is provided a process for the preparation of ethyl trifluoroacetate comprising in a first stage, contacting trifluoroacetic acid with a slight excess of ethanol in the presence of concentrated sulfuric acid and a solvent for a time sufficient to achieve a first esterification. The solvent has a boiling point higher than that of trifluoroacetic acid, a specific gravity relative to water less than 1 and does not form an azeotrope with ethyl trifluoroacetate. Thereafter, a phase separation is carried out and the sulfuric layer is removed.

As embodied herein and referring to FIG. 1, to shift the reaction equilibrium during the first stage of the reaction, excess ethanol will be introduced at 4 in an amount up to a maximum of 10% over the stoichiometric amount and preferably approximately 5% over the stoichiometric amount.

The reaction is carried out in the presence of sulfuric acid shown at 6 which acts as dehydrating agent for the reaction medium and also acts as catalyst.

To carry out dehydration, the sulfuric acid employed is preferably the commercial concentrated acid. It is preferably employed in a proportion representing at least 3% by weight of the trifluoroacetic acid employed. More preferably, the quantity of sulfuric acid ranges from 5.5% to 10%, most preferably, 5.5% to 9%, by weight, relative to the trifluoroacetic acid 8. A larger quantity is not deleterious to the process of the invention, but does not offer any additional advantage. The quantity of sulfuric acid will be adapted to the profitability of the process by one skilled in the art.

The role of the solvent added at 10 to the reaction medium is to promote the separation of the medium by making the organic phase 12 lighter relative to the inorganic phase 14, which consists of sulfuric acid and water. Thus, the solvent preferably has a specific gravity relative to water less than 1 and must be capable of solubilizing the ester and the unreacted trifluoroacetic acid. To facilitate the subsequent separation of the ester and the solvent, the solvent preferably should not form an azeotrope with the ester and preferably should have a boiling point higher than that of the ester and that of the trifluoroacetic acid.

Toluene and xylene are among the solvents which can be employed in the process of the invention. The solvent will be introduced in a quantity by weight which is preferably at least equal to twice that of trifluoroacetic acid and more preferably in a quantity representing approximately 300 g per mole of the trifluoroacetic acid introduced.

During the separation of the mixture 11 obtained after reaction of the acid with the ethanol, there is no loss of trifluoroacetic acid into the inorganic phase 14. The presence of the solvent promotes passage of trifluoroacetic acid into the organic phase 12. The majority of the excess ethanol employed remains in the inorganic phase 14 and is removed.

Since ethanol is a much less expensive starting material than trifluoroacetic acid, it is preferable to remove the ethanol.

In accordance with the invention, there is provided a second stage which comprises introducing an additional quantity of sulfuric acid and trifluoroacetic acid to the mixture from the first stage and reacting for a time sufficient to achieve a second esterification. A phase separation is then carried out and the sulfuric layer is removed.

As embodied herein and referring to FIG. 1, in the second stage, the organic phase 12, which contains a slight excess of ethanol, is contacted with an additional quantity of trifluoroacetic acid 16 and sulfuric acid 18. The quantity of trifluoroacetic acid introduced must enable the entire amount of ethanol remaining in the medium to be esterified. Thus, at least 10% by weight of trifluoroacetic acid is added relative to the trifluoroacetic acid introduced during the first stage. Preferably, a quantity ranging from 10% to 20% by weight of the first stage trifluoroacetic acid is added. More preferably, this quantity will range from 15% to 20%.

The quantity of concentrated sulfuric acid introduced during the second stage is preferably at least 5% by weight relative to the combined weight of trifluoroacetic acid and ethanol introduced during the first stage and more preferably approximately 7%.

After the final reaction of the remaining ethanol and the trifluoroacetic acid, the mixture 22 settles and becomes separated into two phases. The lower phase 24, which consists of sulfuric acid and the water formed by the esterification, may be recycled, if desired, into the first stage of the process according to the invention.

In accordance with the invention there is provided a third stage which comprises distilling the mixture obtained in the second stage to recover pure ethyl trifluoroacetate.

As embodied herein and referring to FIG. 1, the organic phase 26 of the mixture, which consists of the ester, the excess trifluoroacetic acid and the solvent, undergoes a distillation stage during which three fractions are separated.

An overhead fraction 30 is obtained containing a mixture, distilled at a temperature ranging from 53° to 60° C., which consists of a water phase 32 and an ester phase 34 which settles easily. The water phase 32 is removed and the ester phase 34 is recycled into the second stage of the process.

A second fraction 36 consists of ethyl trifluoroacetate having a purity greater than 99% and a boiling point of 60° C.

A third fraction 38 consists essentially of an ethyl trifluoroacetate-trifluoroacetic acid azeotrope distilled from 60° to 135° C. and having a boiling point of 73° C., a small amount of ester and a small amount of solvent and can be recycled, if desired, into the second esterification stage.

The distillation residue 40, essentially consisting of solvent, may be reintroduced, if desired, into the first stage.

In accordance with the present invention there may be provided an additional esterification step in the first stage of the process. This step comprises adding an additional amount of sulfuric acid to the reaction medium and reacting for a period of time sufficient to complete the first esterification. A second phase separation is then carried out to remove the resulting sulfuric layer.

In the second esterification step in the first stage, the sulfuric acid is preferably employed in a proportion representing at least 3% by weight of the trifluoroacetic acid employed and more preferably ranges from 5.5% to 10%, most preferably, 5.5% to 9%, by weight relative to the trifluoroacetic acid.

Figure 2:
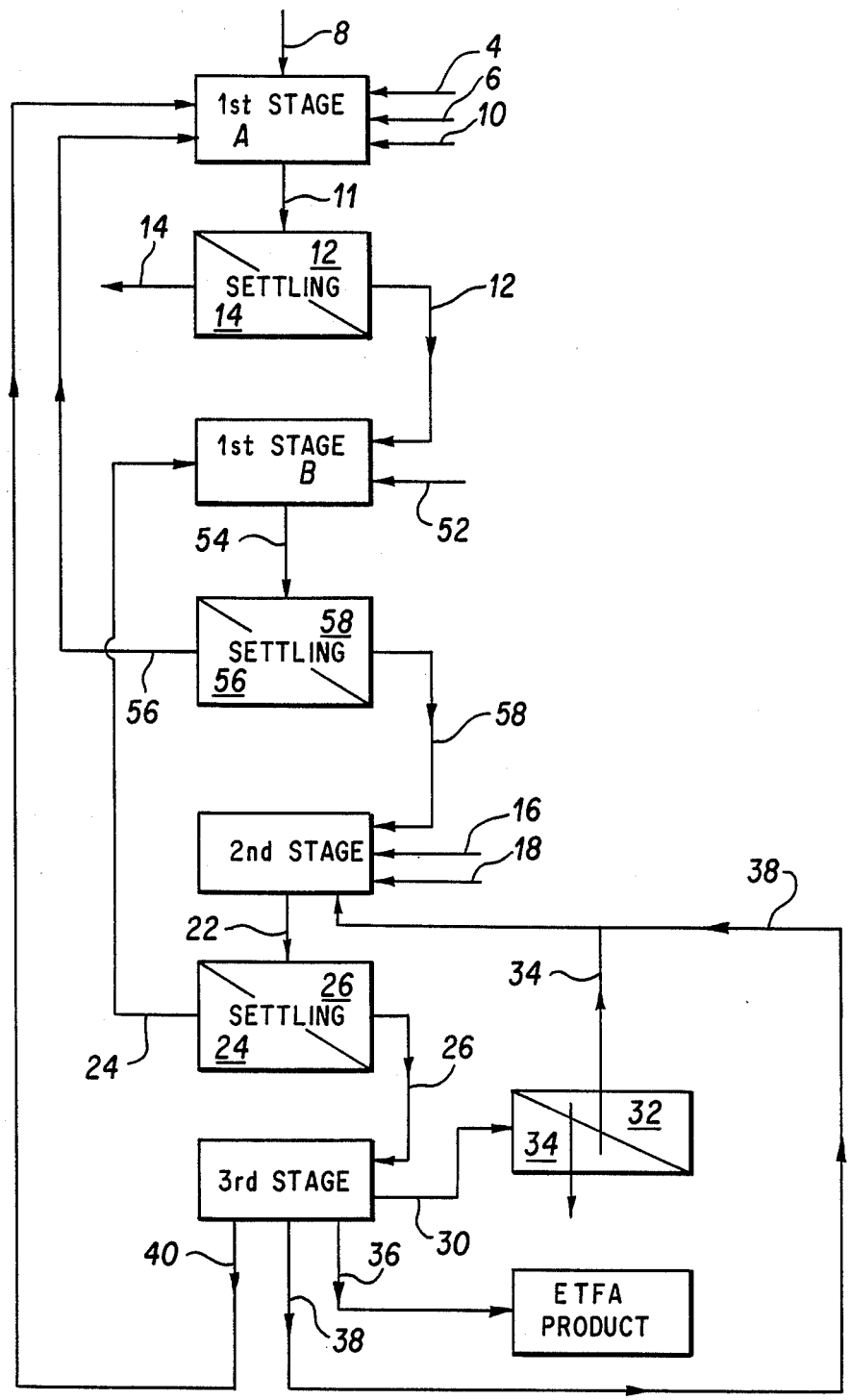
FIG. 2 is a flow diagram of a second embodiment of the invention process having an additional esterification step in the first esterification stage.

As embodied herein and referring to FIG. 2, the second esterification step is labeled first stage B. This step includes a second addition of sulfuric acid 52 to the reaction medium. The mixture 54 formed by this reaction is then separated, with the inorganic phase 56 removed for recycle to first stage A with the organic phase 58 being introduced into the second stage.

The invention will be described more completely with reference to the following examples which are not to be regarded as limiting the scope of the invention.

In the following examples, the trifluoroacetic acid is referred to as TFA and ethyl trifluoroacetate as ETFA.

EXAMPLE 1

This example, illustrated in FIG. 2, utilizes toluene as the auxiliary solvent, consists of three cycles and contains two esterification steps in the first stage.

Cycle I

A 2 liter laboratory reactor equipped with stirring, heating, regulating, distilling ("Oldershaw" type laboratory column containing 30 actual plates—approximately 22 theoretical plates) and condensing devices was employed. The reactor was fitted with a device which enables phase separation to occur and liquids to be drawn off.

1st stage A 3 moles of TFA (8) followed by 3.15 moles of ethanol (4) were introduced in sequence into the reactor with slight stirring and over the course of approximately 0.5 hour. This caused the temperature to rise by approximately 25° C. 30 g of 98% H$_2$SO$_4$ (6) and 12 g of water were then added to approximate and simulate the equilibrium system which occurs when the sulfuric phase from the second stage, already containing water, is introduced instead of pure H$_2$SO$_4$. The mixture was heated under reflux for 1 hour, the heating was then discontinued and 900 g of pure toluene (10) were introduced. The mixture was stirred for approximately 10 min., the stirring was then discontinued and the mixture was allowed to settle. The two liquid layers separated from each other almost immediately and completely (no cloudiness).

The lower layer (14), which weighed 84 g, was drawn off.

1st stage B 30 g of 98% pure $H_2SO_4$ (52) were added to the reactor and the contents were heated under reflux for 1 hr. and 30 min., with stirring, then cooled to 20° C., allowed to settle, and the lower layer weighing 43 g was drawn off and retained (56).

2nd stage 30 g of 98% $H_2SO_4$ (18) and 0.5 mole of TFA (16) were added again. The mixture was heated under reflux, with stirring, for 1 hr. and 30 min. The temperature reached 59° C. at the top of the column and 86° C. in the boiler. After cooling to 70° C., a lower layer weighing 30 g was drawn off and retained (24).

3rd stage—distillation

With a reflux ratio of approximately 4, a first 26 g fraction (30) releasing 1 g of water was distilled between 58° and 60° C. Analysis by sampling indicated 1.5% ethanol, 2% TFA and 36% ETFA. After sampling, the remaining 18 g (34) were recycled into the second stage boiler.

A 288 g fraction (36) containing 99.5% ETFA, which constitutes ester production, was then distilled at a fixed temperature of 60° C.

A fraction (38) weighing 196 g, containing 0.53 mole of TFA was then separated from 60° to 110° C., with a plateau at 73° C. and this fraction (38) was stored.

The mixture was then allowed to cool.

Cycle II

To the liquid (40) (essentially toluene) remaining in the reactor:

1st stage A 3 moles of TFA (8), 3.15 moles of ethanol (4) and the fraction (56) were added. After heating under reflux for 1 hour and cooling, a lower layer (14) weighing 94 g was separated and removed.

1st stage B

The retained lower layer (24) was added again, the mixture was heated under reflux for 1 hr. and 30 min., with stirring and operating as in the first stage, and the lower layer (56) weighing 33 g was separated and stored.

2nd stage 30 g of 98% pure $H_2SO_4$ (18) and the fraction 38 referred to above were added. The mixture was heated under reflux, with stirring, for 1 hr. and 30 min.

Operating as before, a lower layer weighing 31 g (24) was collected.

3rd stage—distillation

A fraction (30) distilled at 59°—60° C. at the top of the column was obtained which separated into 7 g of water and 13 g of an organic layer (34). The analysis of 34 showed that it consisted of 97% ETFA, 0.28% TFA, 0.99% ethanol and 0.48% toluene.

Then, at 60° C., a 417 g fraction (36) which contained 99.7% ETFA, 0.1% ethanol, 0.04% toluene and 0.15% TFA was separated.

From 60° to 110° C., with a plateau at 73° C., a 172 g fraction (38) which contained 0.49 mole of TFA was separated.

The distillation was then stopped and the mixture 40 was allowed to cool.

Cycle III

1st stage A

The reaction was carried out as in the previous cycle by adding 3 moles of TFA (8), 3.15 moles of ethanol (4) and lower layer (56) to the liquid (40) which remained in the reactor. The acid aqueous layer removed (14) weighed 79 g.

1st stage B

Lower layer (24) was added and the procedure was carried out as before. An acid aqueous layer which weighed 38 g (56) was separated.

2nd stage

The fraction 38 and a fresh quantity of 30 g of $H_2SO_4$ (18) were added this time. The acid layer which weighed 31 g (24) was separated.

3rd stage—distillation

A first fraction (30) distilling from 57° to 60° C. was obtained consisting of 5 g of water and 28 g of a product which contained 98.6% ester (34). This was followed by the ester fraction (36) distilled at a fixed temperature of 60° C., which weighed 417 g and contained, according to analysis, 99.7% ester, 0.09% ethanol, 0.03% toluene and 0.06% TFA. The final fraction (38) distilled from 60° to 110° C., weighed 157 g and contained: 43% TFA, 54% ETFA and approximately 3% toluene. This fraction as well as the first 28 g fraction (34) can be used in a new cycle.

The distillation residue (40) weighed 850 g.

EXAMPLE 2

This example, illustrated in FIG. 1, utilizes toluene as the solvent, consists of three cycles and contains one esterification step in stage 1. The same quantities of TFA and of ethanol as in the previous example were reacted in each esterification cycle in the same manner. The results of this example are related to the previous example; some fractions which can be recycled and the solvent charge which remained from the 3rd stage distillation were utilized from the previous example.

Cycle I

1st stage 3 moles of TFA (8), 3.16 moles of ethanol (4) and lower layer (24) were added to the distillation residue (40) from the last cycle of the previous example. After the usual procedure, an acid aqueous fraction (14) which weighed 70 g, and contained 0.47% total F and less than 1 mg/kg $F^-$ ions was separated.

2nd stage

A fresh quantity of 30 g of $H_2SO_4$ (18) and fraction 38 representing 0.59 mole of TFA were introduced and a lower layer (24) which weighed 46 g was then separated.

3rd stage—distillation

The distillation gave a first fraction (30) distilled from 58° to 60° C. which contained 7 g of water and 18 g of ester (34), a second fraction (36) distilled at 60° C. which weighed 411 g, and a third fraction (38) distilled from 61° to 110° C., which weighed 159 g, and contained 0.37 mole of TFA.

Cycle II

1st stage

The reaction was carried out as above, using lower layer 24 as acid. An aqueous acid layer 14 which weighed 90 g and contained 0.22% total F and less than 1 mg/kg F$^-$ ions was separated.

2nd stage 34, 38 which contained an excess of TFA (0.37 mole) and a fresh quantity of 30 g of $H_2SO_4$ (18) were added. A layer which weighed 43 g (24) was separated.

3rd stage—distillation

The first fraction (30) gave 4 g of water and 45 g (34) of ester which can be recycled. The second fraction (36), obtained at 60° C., weighed 453 g. A fraction (38) which weighed 91 g and contained 0.29 mole of TFA was then separated.

Cycle III

1st stage

The reaction was carried out as above, using 24 as the $H_2SO_4$ source. An aqueous layer (14) which weighed 84 g was separated.

2nd stage 34, 38, 0.20 mole of fresh TFA (16) and 30 g of $H_2SO_4$ (18) were added.

The aqueous acid layer (14) which was separated weighed 36 g.

3rd stage—distillation

Three fractions were separated. A first fraction (30) distilled from 57° to 60° C., weighed 41 g and contained 98.3% ETFA, a second fraction (36) which weighed 426 g, distilled at 60° C. and a third fraction (38) distilled from 60° to 110° C., with a plateau at 73° C., weighed 118 g and contained 28.2% TFA, 44.4% ETFA and 27.3% toluene.

EXAMPLE 3

In this example, illustrated in FIG. 1, two cycles were performed in the laboratory apparatus, each containing one esterification in stage 1, with toluene being replaced by technical grade xylene.

Cycle I

1st stage 3 moles of TFA (8) and 3.15 moles of ethanol (4) in the presence of 900 g of technical grade xylene (10) and 30 g of concentrated $H_2SO_4$ (6) were reacted. The mixture was heated under reflux with stirring for 1 hr. and 30 min. The temperature in the boiler was 78° C. The mixture (11) was then cooled to approximately 40° C. and allowed to settle. The lower layer (14) which weighed 78 g was separated.

2nd stage 30 g of concentrated $H_2SO_4$ (18) and 0.5 mole of TFA (16) were added to the reaction medium and the mixture was heated under reflux, with stirring, for 1 hr. and 30 min. The mixture (22) was then cooled to approximately 50° C. was and allowed to settle and the lower layer weighing 36 g was separated, this being fraction 24.

3rd stage—distillation

An overhead fraction 30 distilled from 53° to 60° C. is separated, after condensation, into a lower ester layer (34) which weighed 137 g and an upper layer (32) which weighed 7 g and was discarded. A fraction (36) which weighed 286 g and contained 99.5% ETFA was then collected at a 60° C. plateau, followed by a fraction (38) which distilled from 60° to 135° C., weighed 91 g and contained, according to analysis, 0.42 mole of TFA. The operation was discontinued, and the boiler reactor was cooled.

Cycle II

1st stage 3 moles of TFA (8), followed by 3.15 moles of ethanol (4) and the acid fraction (24) weighing 36 g were introduced into the liquid remaining in the reactor at the end of the previous cycle. The reaction was carried out as in cycle I and an aqueous/sulfuric layer (14) which weighed 91 g at 20° C. was separated.

2nd stage

The fractions (34) and (38) from the previous cycle, followed by 30 g of concentrated $H_2SO_4$ (18) and 0.08 mole of TFA (16) were added to the contents of the reactor. At reflux, the temperature reached 56° C. at the top of the column and 82° C. in the boiler. After cooling to approximately 40° C., the lower layer (24) which had settled, was separated and weighed 33 g.

3rd stage—distillation

A fraction (30) distilled from 55° to 60° C., which separated into 3 g of water (upper layer 32) and 141 g of ester (34) was obtained which contained 99.4% of ETFA. A fraction (36) distilled at 60° C., which weighed 400 g and contained 99.7% ETFA was obtained. A fraction (38) distilled from 60° to 137° C. which weighed 103 g and contained, according to analysis, 0.44 mole of TFA, was also obtained.

I claim:

1. A process for the preparation of ethyl trifluoroacetate, comprising:
   in a first stage, contacting trifluoroacetic acid with a slight excess of ethanol in the presence of concentrated sulfuric acid and a solvent for a time sufficient to achieve a first esterification, said solvent being present in an amount sufficient to solubilize trifluoroacetic acid and ethyl trifluoroacetate, having a boiling point higher than that of trifluoroacetic acid, and having a specific gravity less than 1 and which solvent does not form an azeotrope with ethyl trifluoroacetate and thereafter carrying out a phase separation and removing the resulting sulfuric layer;
   in a second state, introducing an additional quantity of sulfuric acid and trifluoroacetic acid and reacting for a time sufficient to achieve a second esterification and then carrying out a phase separation and removing the resulting sulfuric layer; and
   in a third stage, distilling the mixture obtained from the second stage to recover ethyl trifluoroacetate.

2. The process of claim 1 further comprising adding in said first stage a second quantity of concentrated sulfuric acid after said phase separation and reacting for a time sufficient to complete said first esterification, and then carrying out a second phase separation and removing the resulting sulfuric layer.

3. The process of claim 2, wherein said excess of ethanol ranges from 2% to 10% relative to the stoichiometric amount.

4. The process of claim 3, wherein said excess of ethanol is approximately 5%.

5. The process of claim 2 wherein each of said quantities of concentrated sulfuric acid introduced in said first stage is at least 3% by weight relative to the trifluoroacetic acid introduced in said first stage.

6. The process of claim 5, wherein each of said quantities of concentrated sulfuric acid introduced in said first stage ranges from 5.5% to 10% by weight of the trifluoroacetic acid introduced.

7. The process of claim 2, wherein said solvent is selected from the group consisting of toluene and xylene.

8. The process of claim 7, wherein said solvent is toluene.

9. The process of claim 8, wherein the weight ratio of said toluene employed relative to said trifluoroacetic acid introduced is at least 2:1.

10. The process of claim 9, wherein approximately 300 g of said toluene is employed per mole of trifluoroacetic acid introduced.

11. The process of claim 2, wherein said additional quantity of sulfuric acid introduced during the second stage is at least 5% by weight of the combined weight of trifluoroacetic acid and ethanol introduced during the first stage.

12. The process of claim 11, wherein said additional quantity of sulfuric acid introduced during the second stage is approximately 7% by weight of the quantity of trifluoroacetic acid and ethanol introduced during the first stage.

13. The process of claim 2, wherein said additional quantity of trifluoroacetic acid introduced during the second stage ranges from 10% to 20% by weight relative to the trifluoroacetic acid introduced during the first stage.

14. The process of claim 13, wherein said additional quantity of trifluoroacetic acid introduced during the second stage ranges from 15% to 20% by weight relative to the trifluoroacetic acid introduced during the first stage.

15. The process of claim 2, wherein said third stage distillation produces: a first fraction consisting essentially of ethyl trifluoroacetate and water, a second fraction consisting essentially of ethyl trifluoroacetate, a third fraction consisting essentially of a mixture of trifluoroacetate and ethyl trifluoroacetate and a remainder consisting essentially of toluene.

16. The process of claim 15, further comprising separating ethyl trifluoroacetate from said first fraction and recycling said ethyl trifluoroacetate to said second stage esterification reaction.

17. The process of claim 15, further comprising recycling said third fraction from said third stage distillation to said second stage esterification reaction.

18. The process of claim 15, further comprising recycling said remainder from said third stage distillation into said first stage first esterification.

19. The process of claim 2, further comprising recycling said sulfuric layer from said second phase separation in said first stage into said first esterification reaction in said first stage.

20. The process of claim 2, further comprising recycling said sulfuric layer from said second stage phase separation into said second esterification reaction in said first stage.

21. The process of claim 1, further comprising recycling said sulfuric layer from said second stage phase separation into said first stage esterification reaction.

22. The process of claim 2, wherein said ethyl trifluoroacetate has a purity greater than 99%.

23. The process of claim 1, wherein said excess of ethanol ranges from 2% to 10% relative to the stoichiometric amount.

24. The process of claim 1, wherein said excess of ethanol is approximately 5%.

25. The process of claim 1 wherein said quantity of concentrated sulfuric acid introduced in said first stage is at least 3% by weight relative to the trifluoroacetic acid introduced.

26. The process of claim 25, wherein said quantity of concentrated sulfuric acid introduced in said first stage ranges from 5.5% to 10% by weight of the trifluoroacetic acid introduced.

27. The process of claim 1, wherein said solvent is selected from the group consisting of toluene and xylene.

28. The process of claim 27, wherein said solvent is toluene.

29. The process of claim 28, wherein the weight ratio of said toluene employed relative to said trifluoroacetic acid introduced is at least 2:1.

30. The process of claim 29, wherein approximately 300 g of said toluene is employed per mole of trifluoroacetic acid introduced.

31. The process of claim 1, wherein said additional quantity of sulfuric acid introduced during the second stage is at least 5% by weight of the combined weight of trifluoroacetic acid and ethanol introduced during the first stage.

32. The process of claim 31, wherein said additional quantity of sulfuric acid introduced during the second stage is approximately 7% by weight of the quantity of trifluoroacetic acid and ethanol introduced during the first stage.

33. The process of claim 1, wherein said additional quantity of trifluoroacetic acid introduced during the second stage ranges from 10% to 20% by weight relative to the trifluoroacetic acid introduced during the first stage.

34. The process of claim 33, wherein said additional quantity of trifluoroacetic acid introduced during the second stage ranges from 15% to 20% by weight relative to the trifluoroacetic acid introduced during the first stage.

35. The process of claim 1, wherein said third stage distillation produces: a first fraction consisting essentially of ethyl trifluoroacetate and water, a second fraction consisting essentially of ethyl trifluoroacetate, a third fraction consisting essentially of a mixture of trifluoroacetate and ethyl trifluoroacetate and a remainder consisting essentially of toluene.

36. The process of claim 35, further comprising separating ethyl trifluoroacetate from said first fraction and recycling said ethyl trifluoroacetate to said second stage esterification reaction.

37. The process of claim 35, further comprising recycling said third fraction from said third stage distillation to said second stage esterification reaction.

38. The process of claim 35, further comprising recycling said remainder from said third stage distillation into said first stage first esterification.

39. The process of claim 1, wherein said ethyl trifluoroacetate has a purity greater than 99%.

* * * * *

UNITED STATES PATENT AND TRADEMARK OFFICE
CERTIFICATE OF CORRECTION

PATENT NO. : 4,879,407

DATED : November 7, 1989

INVENTOR(S) : Louis Amiet

It is certified that error appears in the above-identified patent and that said Letters Patent is hereby corrected as shown below:

Claim 1, line 60, change "state" to --stage--.

Signed and Sealed this

Twenty-sixth Day of March, 1991

Attest:

HARRY F. MANBECK, JR.

*Attesting Officer*  *Commissioner of Patents and Trademarks*